(12) United States Patent
Liu et al.

(10) Patent No.: US 9,402,728 B2
(45) Date of Patent: Aug. 2, 2016

(54) CEMENTLESS HIP STEM

(71) Applicants: Lichu Liu, Maumelle, AR (US); XiaFang Liu, Maumelle, AR (US)

(72) Inventors: Lichu Liu, Maumelle, AR (US); XiaFang Liu, Maumelle, AR (US)

(*) Notice: Subject to any disclaimer, the term of this patent is extended or adjusted under 35 U.S.C. 154(b) by 0 days.

(21) Appl. No.: 14/257,042

(22) Filed: Apr. 21, 2014

(65) Prior Publication Data

US 2014/0330390 A1 Nov. 6, 2014

Related U.S. Application Data

(60) Provisional application No. 61/818,191, filed on May 1, 2013.

(51) Int. Cl.
*A61F 2/36* (2006.01)
*A61F 2/30* (2006.01)

(52) U.S. Cl.
CPC .............. *A61F 2/3662* (2013.01); *A61F 2/367* (2013.01); *A61F 2/3609* (2013.01); *A61F 2/3676* (2013.01); *A61F 2002/3069* (2013.01); *A61F 2002/30331* (2013.01); *A61F 2002/30507* (2013.01); *A61F 2002/30556* (2013.01); *A61F 2002/30579* (2013.01); *A61F 2002/30841* (2013.01); *A61F 2002/368* (2013.01); *A61F 2002/3631* (2013.01); *A61F 2002/3694* (2013.01)

(58) Field of Classification Search
CPC ..... A61F 2/3662; A61F 2/367; A61F 2/3672; A61F 2002/3674; A61F 2/3676
See application file for complete search history.

(56) References Cited

U.S. PATENT DOCUMENTS

| | | | |
|---|---|---|---|
| 3,670,724 A * | 6/1972 | Bosacco | 606/64 |
| 4,919,673 A | 4/1990 | Willert | |
| 4,921,501 A | 5/1990 | Giacometti | |
| 5,156,627 A | 10/1992 | Amstutz | |
| 5,725,595 A | 3/1998 | Gustilo | |
| 5,888,208 A * | 3/1999 | Ro | 623/23.15 |
| 6,007,581 A | 12/1999 | Nobel | |
| 6,034,295 A * | 3/2000 | Rehberg et al. | 623/23.49 |
| 6,409,768 B1 * | 6/2002 | Tepic et al. | 623/23.27 |
| 7,947,135 B2 | 5/2011 | Fonte | |
| 8,252,062 B2 | 8/2012 | Bandoh | |
| 8,709,092 B2 * | 4/2014 | Segina et al. | 623/22.12 |
| 2005/0261778 A1 * | 11/2005 | Zelener et al. | 623/23.23 |
| 2008/0051912 A1 * | 2/2008 | Hollawell | 623/54 |

* cited by examiner

*Primary Examiner* — Yashita Sharma
*Assistant Examiner* — Daniel Bissing
(74) *Attorney, Agent, or Firm* — Daniel Boudwin; Global Intellectual Property Agency

(57) ABSTRACT

A cementless femoral stem prosthesis for use in hip replacement surgery is disclosed. The stem has a collar and a body having a fixed end and a shank end. The shank end is divided into a pair of adjustable endosteal plates that are secured to the cortical bone of the femur by screws. The present invention provides an improved femoral stem structure because the screws through the endosteal plates transfer the load to the cortical bone rather than the cancellous bone, the medial endosteal plate has a plurality of spurs to engage with the cancellous bone to increase the number of stress-strain points, and the collar transfers the load directly to the cortical bone. All of these features work in tandem to reduce the risk of stress shielding, bone resorption, prosthetic loosening, and other difficulties associated with femoral stem prostheses.

11 Claims, 7 Drawing Sheets

CEMENTLESS HIP STEM

CROSS REFERENCE TO RELATED APPLICATION

This application claims the benefit of U.S. Provisional Application No. 61/818,191 filed on May 1, 2013, entitled "Cementless Hip Stems." The above identified patent application is herein incorporated by reference in its entirety to provide continuity of disclosure.

BACKGROUND OF THE INVENTION

1. Field of the Invention

The present invention relates to hip arthroplasty. Specifically, the present invention relates to a prosthetic cementless femoral stem for use in hip replacement strategy.

The hip joint is one of the most important joints in the body, as it is responsible both for supporting the weight of the body and balance. Hip replacement surgery may be necessary when there is avascular necrosis of the femoral head, oseteoarthritis of the hip joint, or a substantial hip fracture, among other reasons. Depending upon the specific issue, one of two types of hip replacement surgery will be used. A hemiarthroplasty is the replacement of the femoral head only. A full hip replacement entails the replacement of both the femoral head and the acetabulum. In either case, a stem prosthesis for the femoral head that is biocompatible, has good mechanical properties, and smoothly interacts with the acetabular articulating surface is necessary.

Several types of femoral head prostheses are currently available in the prior art. Stem prostheses are currently the most common type of femoral head prosthesis, but stemless variations are also available. A femoral stem prosthesis consists of an artificial femoral head that is connecyed to a body portion and that articulates with the acetabulum or the artificial acetabular surface. A femoral stem prosthesis is installed by removing the head and neck portions from the patient's femur and then securing the stem prosthesis within the hollow interior of the femur. Stemless femoral prostheses affix directly to the femoral head, rather than providing a new femoral head. Although less invasive, stemless femoral head prostheses are initially less stable and therefore require longer recovery periods.

Femoral head stem prostheses also come in cemented or cementless variations. Cemented hip stems are secured within the hollow interior of the femur by bone cement. Cementless hip stems are specifically fitted within the femur and often use various techniques to encourage osseointegration with the prosthetic components to secure the device. Results between cemented and cementless hip stems are generally similar if the patient has good enough bone quality to accept a cementless prosthesis, but cement can degrade over time, so cemented stems are generally not used in younger patients.

Currently available hip stem prostheses have a variety of problems. Currently available hip stem prostheses alter the way the body load is distributed through the femur. The body load with a natural, healthy femur is distributed through the femoral head, down the neck, and then downwards through the cortical bone of the femur. The body load with a hip stem prosthesis is distributed from the head, down the neck, and instead then laterally into the cancellous bone because the stem of the prosthesis extends into the femoral canal. Since the hip stem prosthesis changes the normal load distribution in the femur, it can lead to bone resorption and loosening of the prosthesis because bone remodels in response to applied stresses. The process, called stress shielding, occurs when biomechanical forces are transferred to the distal regions of the prosthesis, causing bone to be resorbed in the more proximal portions of the bone near the neck of the prosthesis since the stresses normally present in those portions that stimulate bone growth have been removed by the presence of the prosthesis. When bone is resorbed near the prosthesis neck, the entire prosthesis is no longer secured firmly within the femoral canal and, in serious cases, can result in periprosthetic fracture.

The present invention addresses these issues in multiple ways. First, the cementless hip stem has a collar that directly transfers load to the cortical bone below the neck, reducing the potential for bone resorption in the region of the bone proximal to the femoral head. Second, the cementless hip stem's distal shank end is divided into two endosteal plates that are adjustable to ensure an ideal fit within all types of femurs. Third, the endosteal plates are secured to the cortical bone via a plurality of screws. This helps transfer the body load from the distal end of the prosthesis to the cortical bone, rather than to the cancellous bone. Lastly, the medial endosteal plate has a plurality of spurs that engage with the cancellous bone within the femoral canal to help secure the prosthesis and further distribute the body load. In this regard, the present invention fulfills a substantial need within the art for a cementless hip stem that performs better than the currently available models.

2. Description of the Prior Art

Devices have been disclosed in the prior art that relate to prostheses for use in arthroplasty. These include devices that have been patented and published in patent application publications. These devices generally relate to cemented and cementless hip stem prostheses. The following is a list of devices deemed most relevant to the present disclosure, which are herein described for the purposes of highlighting and differentiating the unique aspects of the present invention, and further highlighting the drawbacks existing in the prior art.

One such device is U.S. Pat. No. 4,919,673 to Willert, which discloses a femoral head prosthesis with a centering rod for guiding the stem during introduction of the prosthesis into the femoral canal. The centering rod is aligned on the central axis of the femoral canal, the bone cement is poured in, and then the hip stem prosthesis is threaded onto the centering rod and guided into the femoral canal, ensuring proper alignment. This femoral head prosthesis is cemented and thus not secured in the same way as the present invention. Furthermore, this femoral head prosthesis lacks all of the load distribution mechanics that the present invention utilizes, including the collar and the pair of adjustable endosteal plates. Therefore, this invention suffers from all of the problems commonly associated with such implants, such as stress shielding.

Another such device is U.S. Pat. No. 4,921,501 to Giacometti, which discloses a prosthetic femoral stem head having a longitudinally-aligned slot beginning at the distal end of the stem and extending upwards towards the proximal end of the prosthesis at an angle. The distal end of Giacometti has increased resilience, while also being non-resilient relative to lateral loading from the femoral head. This non-resilience to lateral loading is ideally suited for re-operation procedures, which generally extend new prostheses into the increasingly narrow portion of the femoral canal. One embodiment of the present invention is specifically designed for re-operation procedures, like Giacometti, but it has additional elements designed to assist with the displacement of the body load that Giacometti lacks, such as a collar and adjustable endosteal plates.

Yet another such device is U.S. Pat. No. 5,156,627 to Amstutz, which discloses a collarless femoral hip prosthesis. Amstutz describes a series of eight femoral head prostheses that are configured to fit tightly with a wide range of femurs. Although Amstutz seeks to provide increased compatibility with patients of different builds, it nonetheless is not as highly compatible as the present invention because the present invention has a pair of endosteal plates that are freely adjustable and are not limited to merely eight configurations.

U.S. Pat. No. 5,725,595 to Gustilo discloses a cannulated cementless hip stem prosthesis. This invention has three main features. First, a guide rod can be inserted through the cannulated stem portion to precisely align the stem within the femoral canal. Second, Gustilo has a flexible distal portion that deflects loads away from the prosthesis and into the natural bone. Lastly, Gustilo has a roughened interstitial surface for increased interaction with the living femoral bone. The distal portion of the present invention is not flexible, but rather is freely adjustable and transfers load to the cortical bone by being engaged to said bone with screws.

U.S. Pat. No. 6,007,581 to Noble discloses a cementless asymmetric hip stem for hip replacement procedures. Noble's stem has a twist in the mid-stem region, permitting an improved fit while at the same time minimizing enlargement of the femoral canal. Noble further has a slot on the distal end that reduces bending stiffness, like Giacometti. The present invention has an open, separated section at the distal end of the femoral stem prosthesis as well, but this separation is not created to increase flexibility of the distal region. The separated endosteal plates at the distal end of the present invention instead may be adjusted depending upon the width of the individual patient's femur and are not designed to increase flexibility per se.

U.S. Pat. No. 7,947,135 to Fonte discloses a femoral stem prosthesis with a bone-locking mechanism comprised of shape memory material. The shape memory material is deposited within the femoral canal, the hip stem is then placed into position, and then an induced temperature change causes the shape memory material to expand and lock the hip stem prosthesis in place. The bone-locking mechanism is intended to increase primary stability, which leads to a reduction in patient recovery time and allows for greater weight-bearing during recovery. The present invention is locked into place using a variety of means, most notably the cortical screws secured through the endosteal plates, but does not use shape memory material to accomplish the goal of increased stability.

Finally, U.S. Pat. No. 8,252,062 to Bandoh discloses an artificial cementless hip prosthetic stem having an outer body and an inner stem construct. The outer body is a smooth, substantially flat surface that fits within the femoral canal. The inner stem construct then fits within the outer body and an adhesive filler is applied between the outer body and the inner stem construct. The purpose of fitting the hip stem prosthesis within an outer body is to more evenly distribute the forces applied to the prosthesis head throughout the femur, rather than just to the bone in contact with the distal portion of the prosthesis. The present invention has the same goal in more evenly distributing the body load through the cortical bone, but accomplishes this task by directly engaging the endosteal plates with the cortical bone and having a collar that directly transfers load to the cortical bone.

The present invention comprises a new and novel femoral stem prosthesis for use in hip replacement surgery. The cementless hip stem prosthesis has a collar that directly transfers load to the cortical bone near the neck of the device, a plurality of holes in the fixed end of the device to encourage osseointegration with the prosthesis, and a pair of plates secured to the femoral cortical bone that transfer remaining stresses from the distal portion of the prosthesis to the surrounding cortical bone, rather than the cancellous bone. It substantially diverges in design elements from the prior art and consequently it is clear that there is a need in the art for an improvement to existing femoral head prostheses. In this regard the instant invention substantially fulfills these needs.

SUMMARY OF THE INVENTION

In view of the foregoing disadvantages inherent in the known types of arthroscopy prostheses now present in the prior art, the present invention provides a new cementless femoral stem prosthesis wherein the same can be utilized for providing convenience for the user when undergoing hip replacement surgery.

It is therefore an object of the present invention to provide a new and improved cementless femoral stem prosthesis device that has all of the advantages of the prior art and none of the disadvantages.

It is another object of the present invention to provide a femoral stem prosthesis that does not need to be cemented within the femoral canal.

Another object of the present invention is to provide a femoral stem prosthesis that is stable and provides short recovery periods for patients.

Yet another object of the present invention is to provide a femoral stem prosthesis that eliminates or reduces the stress shielding effect, which can lead to a variety of ailments due to the property of bone that it remodels in response to applied stresses.

Yet another object of the present invention is to provide a femoral stem prosthesis that is biocompatible and long-lasting to reduce the chance that hip revision surgery will be necessary.

Yet another object of this invention is to provide a femoral stem prosthesis that is highly adaptable and capable of being used in a wide array of femur types and sizes.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
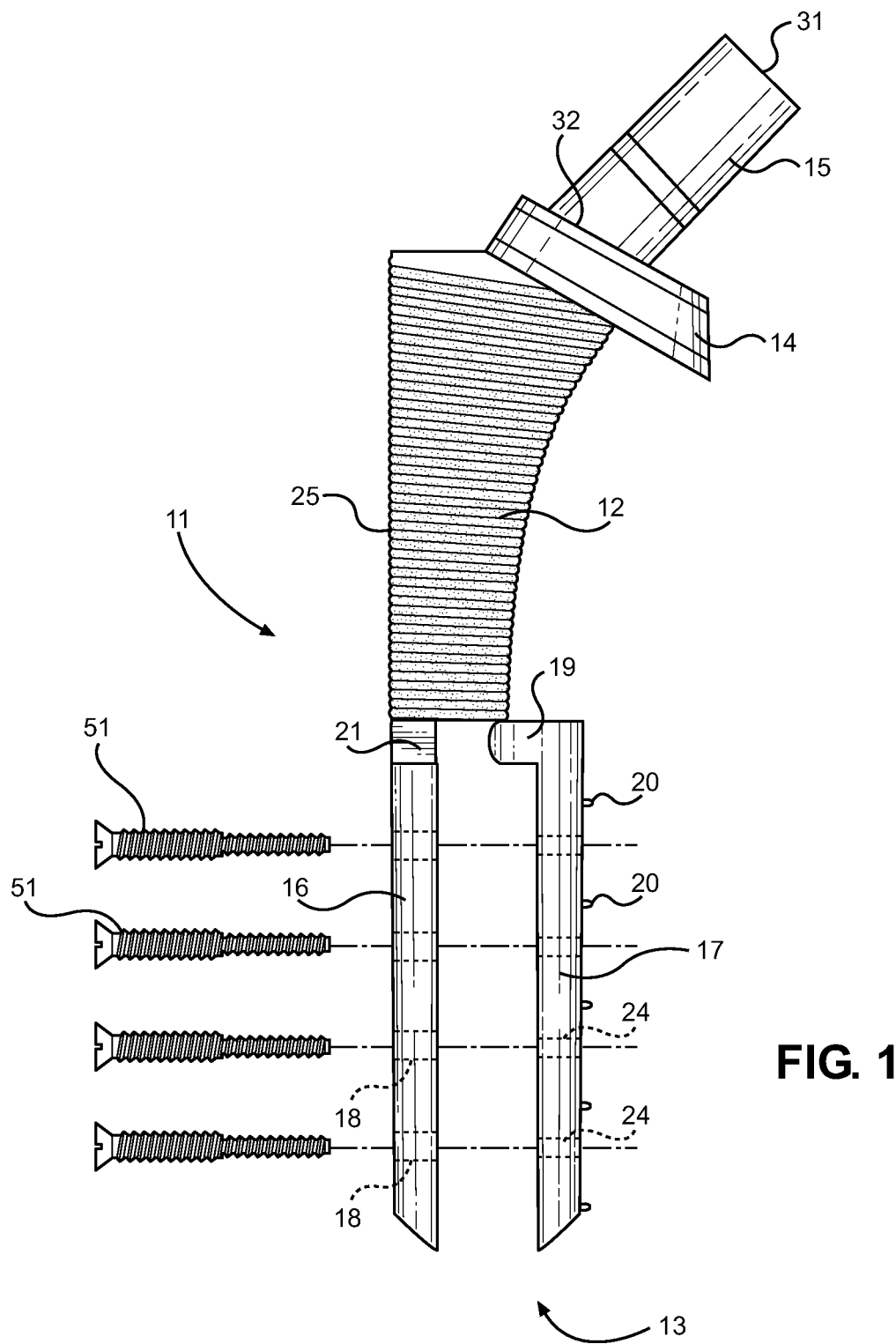
FIG. 1 shows a perspective view of a non-cannulated embodiment of the present invention, without osseointegration holes.

Reference is made herein to the attached drawings. Like reference numerals are used throughout the drawings to depict like or similar elements of the cementless hip stem prosthesis. For the purposes of presenting a brief and clear description of the present invention, the preferred embodiment will be discussed as used for total hip arthroplasty or hemiarthroplasty. The figures are intended for representative purposes only and should not be considered to be limiting in any respect.

Referring now to FIG. 1, there is shown a perspective view of an embodiment of the present invention. The cementless hip stem prosthesis is comprised of a neck 15, a collar 14, and a body 11. The device is constructed of a titanium or cobalt chromium alloy. The body 11 comprises a fixed end 12 and a shank end 13. The neck 15 has an attachment end 31 and a collar end 32. The attachment end 31 of the neck 15 engages with a spherical femoral head, which is not provided in the present invention. The spherical femoral head engages with the living acetabulum or the prosthetic acetabular cup to mimic the ball-and-socket movement between the femoral head and the acetabulum in a natural, healthy joint.

The neck 15 is connected to the collar 14 at the collar end 32. The collar 14 rests directly against the remaining cortical bone of the metaphysis of the femur after the ostectomy of the femoral head. The purpose of the collar 14 is to transfer some of the body load directly to the cortical bone, simulating the force dispersal in a healthy femur, rather than only transferring the force of the body load down the length of the stem into the cancellous bone. It is critical that some of the body load be applied to portions of the cortical bone proximal to the neck 15 because bone remodels in response to applied stresses. If the stresses that are normally present in these regions of the epiphysis and metaphysis of a health femur are removed, then the bone in this region will be resorbed because there will be no, or less, stress applied to this region. This resorption process will increase the size of the aperture into which the prosthesis was inserted, resulting in a loosening of the prosthesis. This process is called stress shielding. Loosening of the prosthesis can lead to pain, damage to the bone near the distal end of the device, and periprosthetic fracture in severe cases.

The collar 14 connects to the body 11 of the device, which is composed of the fixed end 12 located proximally to the collar and the shank end 13 located distally to the collar. The fixed end 12 is of a size and shape such that it may be securely inserted within a femoral canal. The fixed end 12 has a generally tapered configuration, narrowing as it extends distally to the shank end 13. The fixed end 12 has an interstitial surface 25. In the preferred embodiment, the interstitial surface 25 has a roughened or wavy character. This roughened configuration promotes bone integration with the prosthetic because it provides protrusions and valleys with which bone growth can integrate.

The shank end 13 is composed of a lateral endosteal plate 16 and a medial endosteal plate 17. The lateral endosteal plate 16 has a plurality of lateral threaded holes 18 and the medial endosteal plate 17 has a number of medial threaded holes 24 equal to the number of lateral threaded holes 18. The two sets of threaded holes 18, 24 are horizontally aligned when the endosteal plates 16, 17 are engaged with each other. The lateral threaded holes 18 have a first diameter and the medial threaded holes 24 have a second diameter. In the preferred embodiment the second diameter is smaller than the first diameter, such that the threaded holes 18, 24 can receive cortical screws 51 having a complimentary first and second threaded portion. The preferred number of cortical screws 51 and associated threaded holes 18, 24 is 4-8. The endosteal plates 16, 17 are adjustable and can be oriented closer or farther apart. This adjustability allows the hip stem prosthesis to securely fit a wide range of femur sizes. A plurality of spurs 20 are disposed on the medial surface of the medial endosteal plate 17, extending into the surrounding cancellous bone. The spurs 20 assist the device in firmly implanting within the femoral canal and also further assist the distribution of the body load so that it is not all concentrated at the distal tip of the cementless hip stem prosthetic.

An engagement means 19 is disposed on the proximal most end of the medial endosteal plate 17, which is designed to engage with the receiving means 21 on the proximal most end of the lateral endosteal plate 16. In the depicted embodiment, the engagement means 19 comprises a stub that is removably insertable into the receiving means 21, which is comprised of a slot for accepting the stub. The endosteal plates 16, 17 are not permanently affixed to each other in order to permit them to be adjusted in relation to each other. The endosteal plates 16, 17 are affixed to the cortical bone via the cortical screws 51. This, along with the collar 14 directly transmitting the load to cortical bone and the spurs 20 distributing body load with the femoral canal, further allows the forces acted on the femoral head to be distributed throughout the cortical bone to more closely mimic the actual load distribution in a natural, healthy bone. In most hip stem prostheses in the prior art, the stem is merely placed within the femoral canal with little other securement, causing all of the load from the hip joint to be concentrated at the distal end of the stem into the cancellous bone, rather than through the cortical bone.

Figure 2:
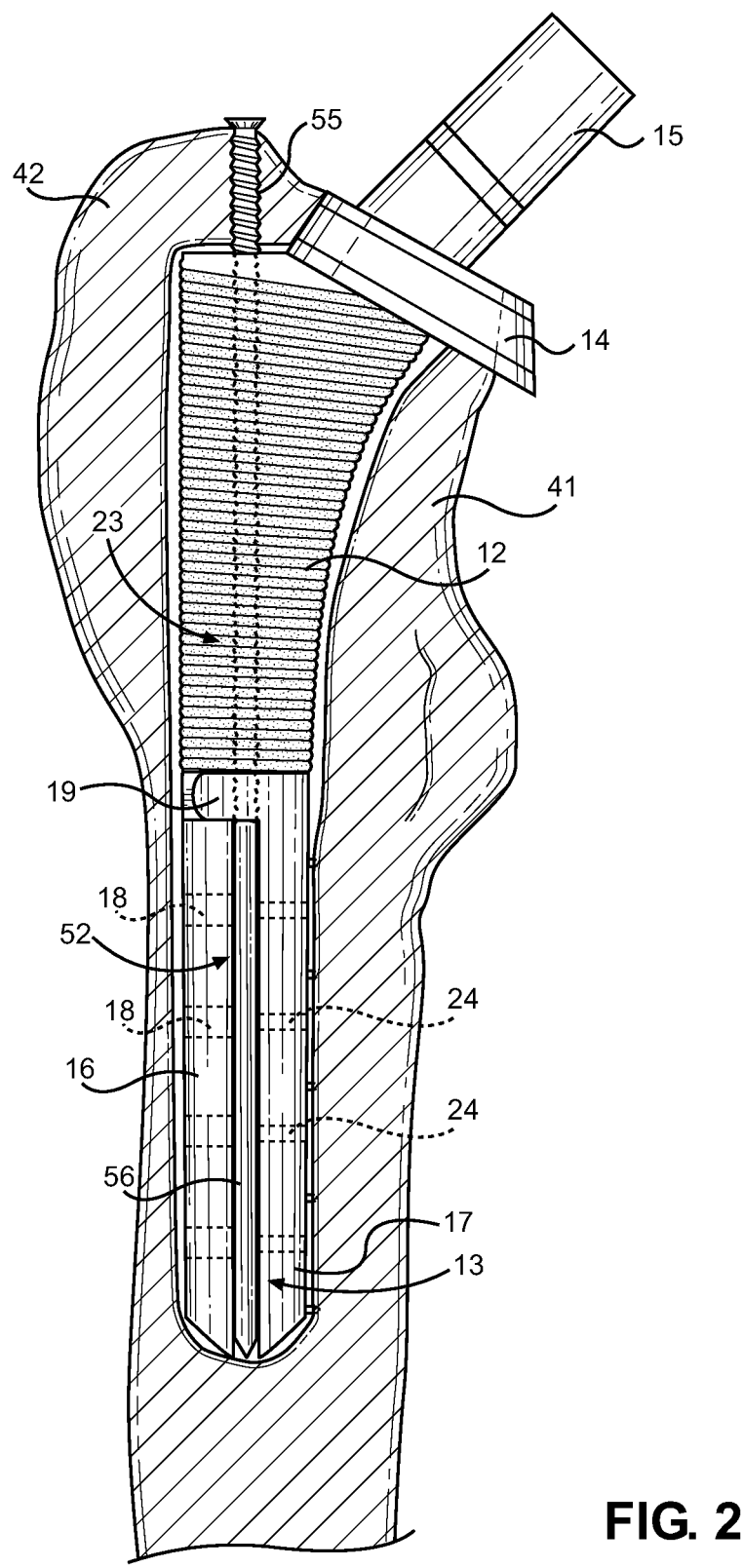
FIG. 2 shows a perspective view of a cannulated embodiment of the present invention, without osseointegration holes, as it appears when installed within a living femur shown in cross section.

Referring now to FIG. 2, there is shown a perspective view of a cannulated embodiment of the present invention as it would appear when installed within a femur, with the femur shown in cross section. As is illustrated, the collar 14 rests directly against the remaining cortical bone 41, transferring some of the body load into the cortical bone, rather than through the stem and into the cancellous bone, to mimic naturally occurring load distribution with a healthy femur and a healthy hip joint. The depicted embodiment provides two separate means for securing the present invention within a living femur. The present invention may be secured via either the threaded holes 18, 24 on the endosteal plates 16, 17 or the inner support means 23.

One method of securing the present invention utilizes the threaded holes 18, 24 in the endosteal plates 16, 17. When installed within a living femur, the cortical screws 51 are screwed through the cortical bone 41 into the threaded holes 18, 24 on the endosteal plates 16, 17. The cortical screws 51 preferably have two different diameters, allowing them to engage with the respective threaded apertures 18, 24. This secures the endosteal plates 16, 17 against the wall of the femoral canal while also securing the plates 16, 17 to the cortical bone. Therefore, the cortical screws 51 are secured to the femoral bone on both sides of the femoral canal. This securement means allows the hip stem prosthesis to sit snugly within the femoral canal while at the same time assisting in distributing the body load into the cortical bone 41. All of these support means allows the stem femoral head prosthesis to be secured without the need for bone cement, which is often used with prior art stem femoral head prostheses.

An alternative method of securing the present invention utilizes the inner support means 23 disposed through the fixed end 12 of the device. In the depicted embodiment, the inner support means 23 comprises a threaded cannula that extends from the most proximal side of the fixed end 12, through the entire fixed end 12, to the shank end 13. A support screw 52 with a complimentary threaded pitch is provided. The support screw has a proximal threaded end 55 and a smooth distal end 56. The proximal threaded end 55 engages with the threading of the internal support means 23, whereas the smooth distal end 56 secures the engagement means 19 in place. The support screw 52 secures the fixed end 12 to the greater trochanter 42, while at the same time extending through the fixed end 12 into the shank end 13 through the engagement means 19 and thereby locking the endosteal plates 16, 17 together. The endosteal plates 16, 17 are held firmly together by the support screw 52 because the support screw 52 holds the engagement means 19 in contact the receiving means 21.

Figure 3:
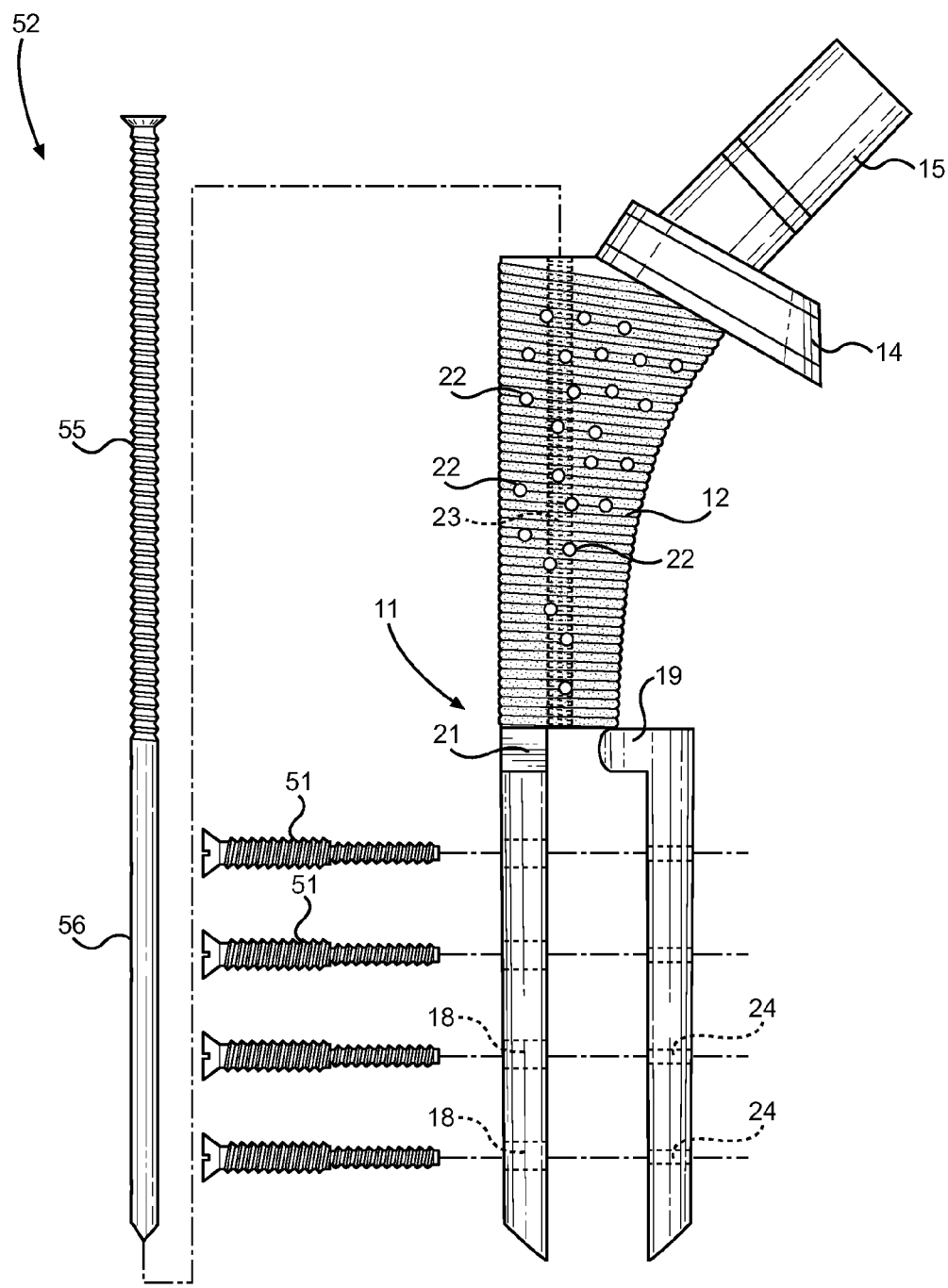
FIG. 3 shows a perspective view of the preferred embodiment of the present invention.

Referring now to FIG. 3, there is shown a perspective view of the preferred embodiment of the present invention. The preferred embodiment is both cannulated and has a plurality of osseointegration holes 22 in the fixed end 12. The fixed end 12 has osseointegration holes 22 distributed proximally and distally, and anteriorly and posteriorly. This permits the cancellous bone to grow throughout the prosthesis, creating an interlinked network of bone. The osseointegration holes 22 act to secure the device even more firmly and allow for improved biocompatibility, since bone can grow into and throughout the prosthesis. Preferably, there will be 6-30 osseointegration holes 22, each having a diameter of 1.5 to 2 mm.

Figure 4:
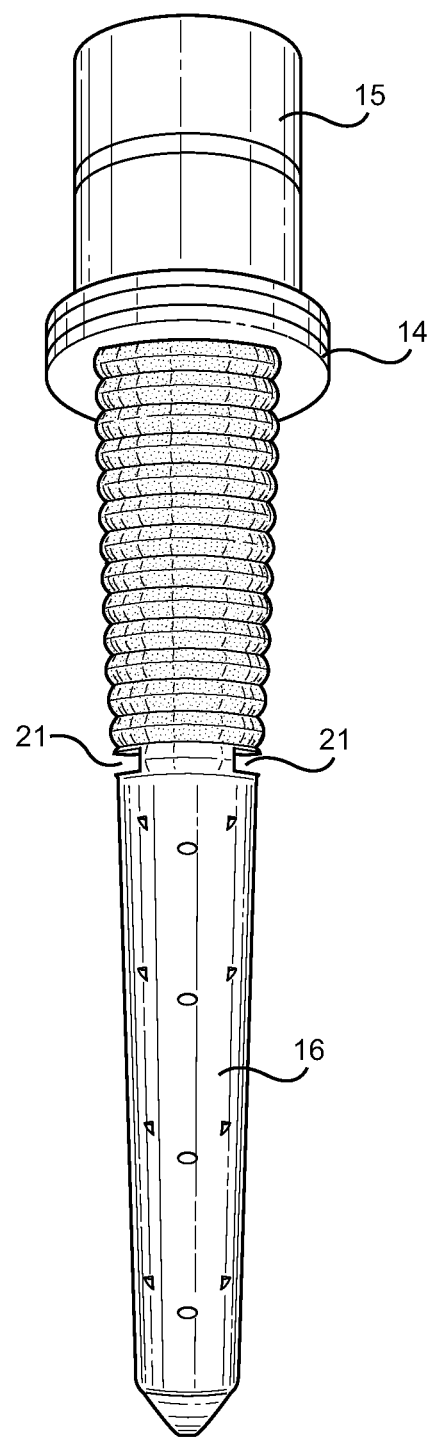
FIG. 4 shows a lateral side view of an embodiment of the present invention.

Referring now to FIG. 4, there is shown a lateral side view of an embodiment of the present invention. The collar 14 is roughly elliptical in shape and extends in an angled medial direction so that it can sit on top of the remaining cortical bone. The receiving means 21 in this embodiment is a slot into which the engagement means of the medial endosteal plate 17 fits. This ensures that that the endosteal plates 16, 17 are properly horizontally aligned without locking them together so that the plates 16, 17 are still adjustable. No claim is made as to the specific structure of the receiving means 21 and the engagement means, as the embodiment depicted herein is merely exemplary. The receiving means 21 and engagements means merely must be designed so that the endosteal plates 16, 17 are able to engage together.

Figure 5:
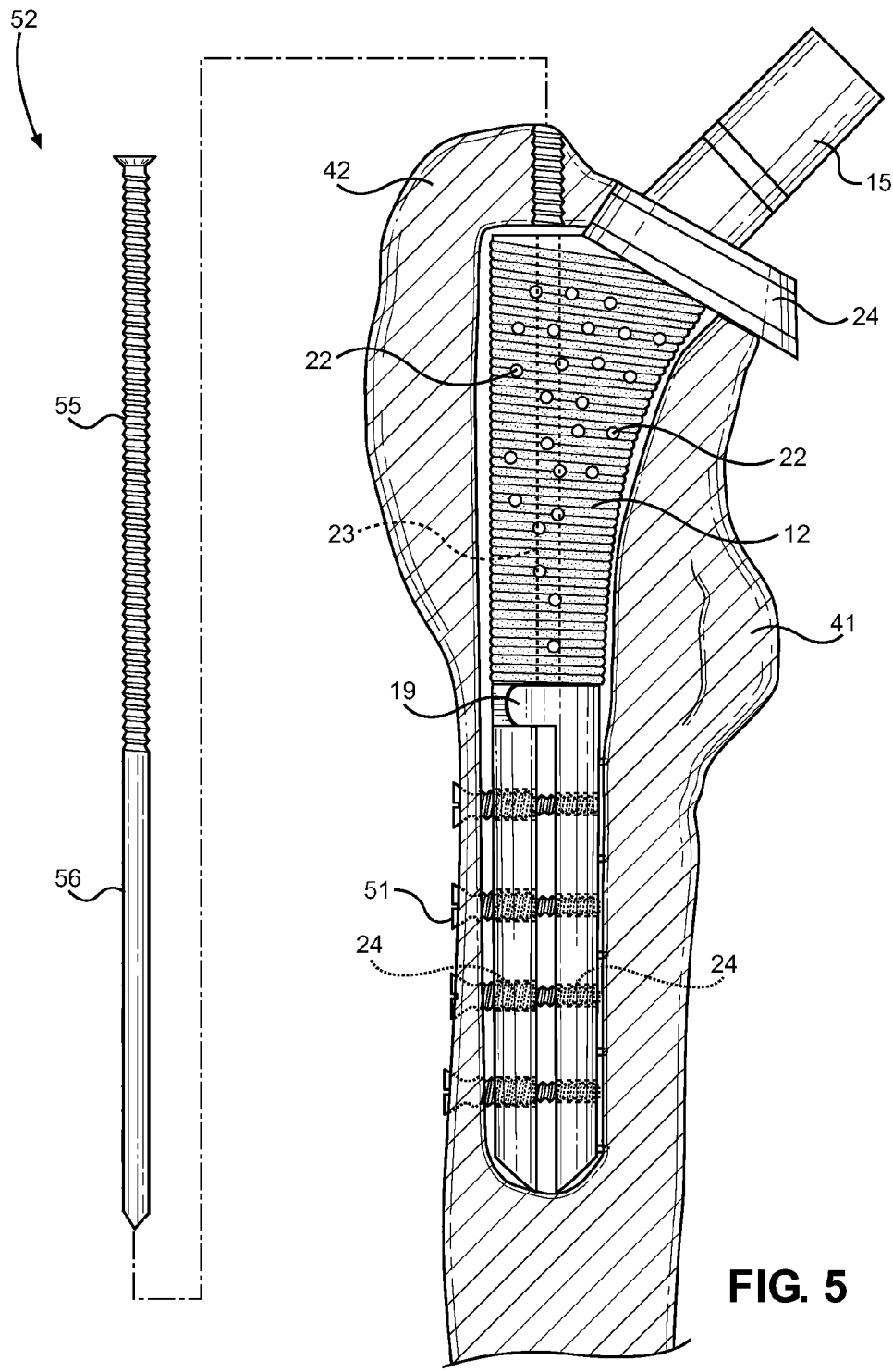
FIG. 5 shows a perspective view of the preferred embodiment of the present invention, as it appears when installed within a living femur shown in cross section.

Referring now to FIG. 5, there is shown a perspective view of the preferred embodiment as it appears when installed within a femur. The preferred embodiment has a cannulated inner support means 23, a plurality of osseointegration holes 22, and a roughened or wavy interstitial surface 25 to promote interaction with cancellous bone within the femoral canal. The preferred embodiment may be secured within the femoral canal by either a support screw 52 through the inner support means 23 or via cortical screws 51 through the threaded holes 18, 24 on the endosteal plates 16, 17. The preferred embodiment of the present invention further has a plurality of osseointegration holes 22 disposed across the surface of the fixed end 12 of the device that allow bone to grow therethrough and create an interlinked network.

Figure 6:
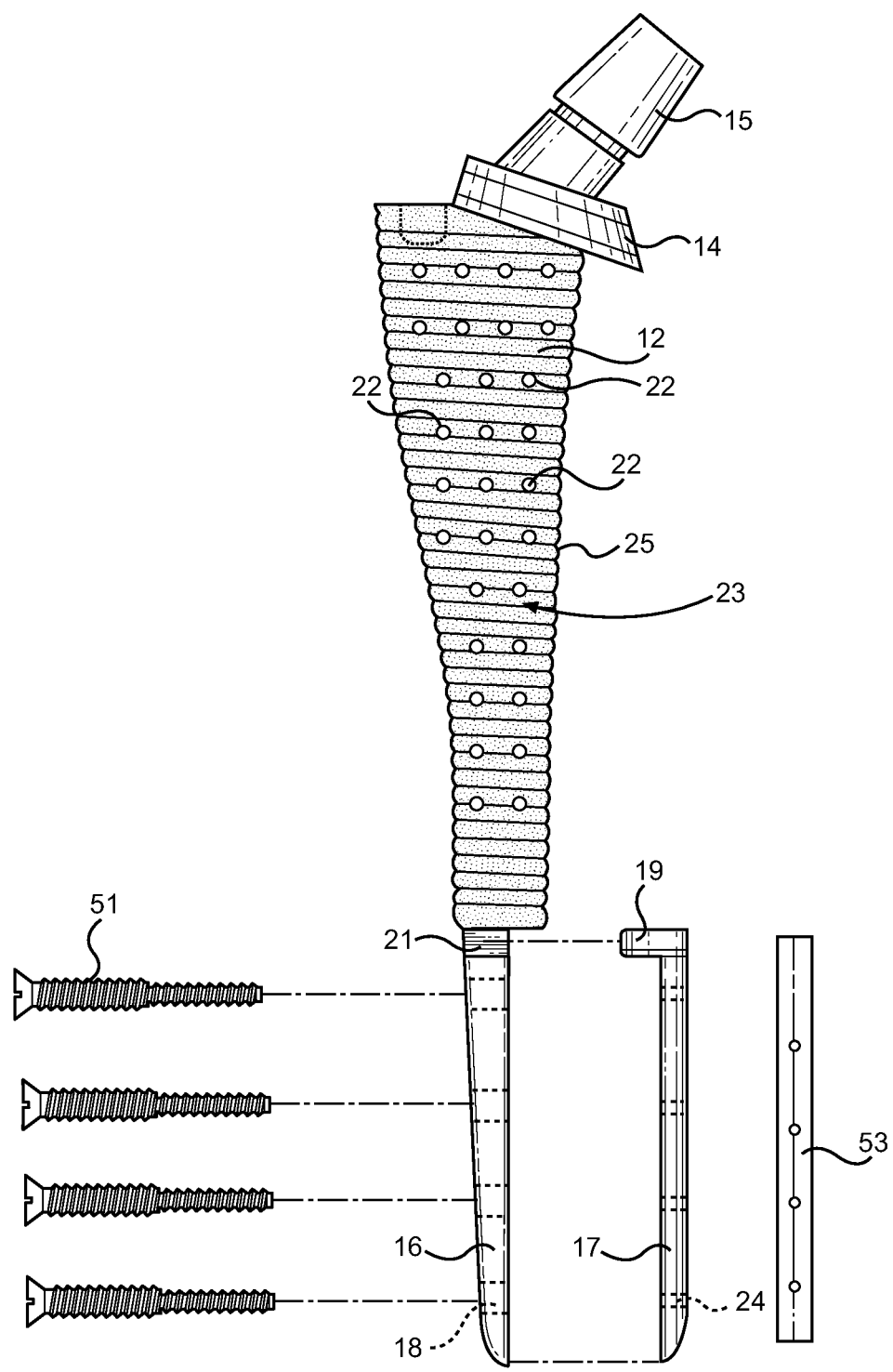
FIG. 6 shows a perspective view of an embodiment of the present invention designed for hip revision surgery.

Referring now to FIG. 6, there is shown a perspective view of an embodiment of the present invention designed for hip revision surgery. The depicted embodiment has a more elongated body 11 than the embodiments depicted in FIGS. 1-5. The elongated body 11 is ideally suited for hip revision surgery because stem prostheses generally need to be inserted deeper into the femoral canal after a first prosthesis has failed, because the first prosthesis usually fails due to periprosthetic loosening. The loosening of the prosthetic can either grind away the edges of the opening into which the stem was inserted or be a symptom of bone resorption due to stress shielding. Therefore, the bone around the initial aperture on the proximal end of the femur is either gone or severely weakened. This requires the femoral head stem prosthesis to be inserted deeper into the narrower portion of the femoral canal, necessitating a narrower, elongated body for the femoral stem prosthesis to be adequately secured.

In embodiments designed for hip revision surgery, the inner support means 23 will ideally not constitute a cannula with a main screw, as in FIGS. 2 and 3, but will instead constitute a plurality of revision screws 54 that are capable of engaging with the osseointegration holes 22 in the fixed end 12. Although the primary purpose of the osseointegration holes is to promote bone growth and interaction with the prosthetic, they also double as a securement means for hip revision surgery embodiments. A revision plate 53 is also provided for embodiments designed for hip revision surgery. The revision plate 53 acts as another securement means when the cortical bone alone is insufficient to hold the device in place. The revision plate is placed 53 on the outer surface of the femoral cortical bone and is threaded to engage with the cortical screws 51. In use, the cortical screws 51 are secured through the patient's cortical bone and into the revision plate 53, thereby securing the revision plate 53 fast against the outer surface of the cortical bone.

Figure 7:
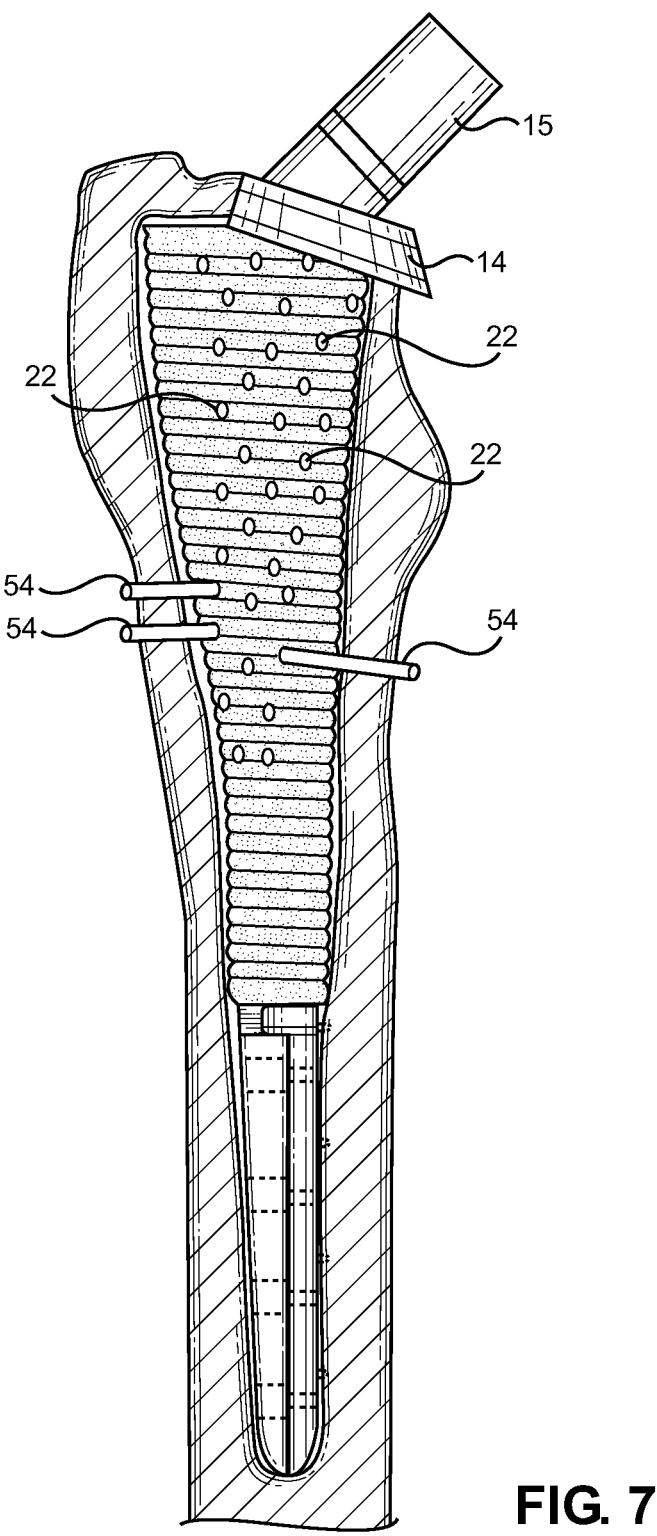
FIG. 7 shows a front view of an embodiment of the present invention designed for hip revision surgery, as it appears when installed into a living femur shown in cross section.

Referring now to FIG. 7, there is shown a perspective view of an embodiment of the present invention designed for hip revision surgery, as it appears when installed within a femur, which is shown in cross section. The osseointegration holes 22 may double as the inner support means if the greater trochanter or other proximal femoral cortical bone is too weak to act as a securement means. A plurality of revision screws 54 are provided for such surgeries that are adapted to engage with the osseointegration holes 22. As many or as few revision screws 54 may be used as necessary to firmly secure the hip stem within the femoral canal.

In use, the present cementless hip stem prosthesis is well suited for minimizing risks associated with hip replacement surgery prostheses, such as stress shielding, bone resorption, and periprosthetic loosening. The present invention reduces the risks by more closely mimicking the body load distribution found in a natural, healthy bone and joint. Current femoral head stem prostheses transfer the body load to the distal end of the stem into the cancellous bone, but in a natural, healthy joint the body load is instead transferred through the cortical bone. The collar directly transfers the load from the hip joint to the cortical bone, the cortical screws through the endosteal plates transfer load from the shank end of the cementless femoral stem prosthesis into the cortical bone, and the spurs further distribute any remaining load evenly throughout the bone, rather than at a single point. Furthermore, the endosteal plates are adjustable, allowing the device to be used in a wide array of sizes and types of femurs. The present invention can also come in different configurations specifically designed for hip revision surgeries.

Overall, it is desired to disclose a cementless hip stem prosthesis that has a collar and a pair of adjustable endosteal plates capable of evenly distributing body load from the hip joint through the femoral cortical bone and fitting into all types and sizes of femurs. It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A cementless femoral stem prosthesis, comprising:
a neck having a collar end and an attachment end;
a collar attached to said neck at said collar end;
a body having a fixed end, a shank end, an interstitial surface, and an inner support, said collar attached to said fixed end;
a lateral endosteal plate attached to said shank end of said body, said proximal endosteal plate having a plurality of lateral threaded holes having a first diameter;
a medial endosteal plate having an inner surface, an outer surface, a plurality of medial threaded holes having a second diameter, and a plurality of spurs on said outer surface;
wherein the plurality of lateral threaded holes are aligned with the plurality of medial threaded holes;
wherein a distance between the lateral endosteal plate and the medial endosteal plate is adjustable via an adjustable connection coupling the lateral endosteal plate and the medial endosteal plate;
a plurality of cortical screws having a first threaded portion adapted to engage with said lateral threaded holes and a second threaded portion adapted to engage with said medial threaded holes.

2. The cementless femoral stem prosthesis of claim 1, further comprising a plurality of osseointegration holes through said fixed end.

3. The cementless femoral stem prosthesis of claim 1, wherein said osseointegration holes have a diameter between 1.5-2 mm and number from 6-30.

4. The cementless femoral stem prosthesis of claim 1, wherein said inner support comprises a threaded cannula extending through said fixed end to said shank end and a support screw adapted to engage with said threaded cannula.

5. The cementless femoral stem prosthesis of claim 2, wherein said inner support comprises a threaded cannula extending through said fixed end to said shank end and a support screw adapted to engage with said threaded cannula.

6. The cementless femoral stem prosthesis of claim 1, wherein the plurality of lateral threaded holes and the plurality of medial threaded holes each number from 4-8.

7. The cementless femoral stem prosthesis of claim 1, further comprising a revision plate adapted to be placed on the outer surface of a femur and having a plurality of threaded apertures adapted to receive said second threaded portion of said cortical screws.

8. The cementless femoral stem prosthesis of claim 1, wherein the adjustable connection comprises a slot disposed on the lateral endosteal plate that is configured to slidably receive a projection extending from the medial endosteal plate.

9. The cementless femoral stem prosthesis of claim 1, wherein the attachment end is configured to engage a femoral head prosthesis.

10. The cementless femoral stem prosthesis of claim 1, wherein the distance between the medial endosteal plate and lateral endosteal plate is adjustable a width of a femoral canal.

11. The cementless femoral stem prosthesis of claim 4, wherein the support screw is configured to lock the medial endosteal plate and the lateral endosteal plate together.

\* \* \* \* \*